United States Patent [19]

Shen et al.

[11] Patent Number: 5,146,011
[45] Date of Patent: Sep. 8, 1992

[54] PREPARATION OF CHLOROHYDRINS

[75] Inventors: Ming Shen, Guilford; John A. Wojtowicz, Cheshire, both of Conn.

[73] Assignee: Olin Corporation, Cheshire, Conn.

[21] Appl. No.: 718,737

[22] Filed: Jun. 21, 1991

Related U.S. Application Data

[63] Continuation-in-part of Ser. No. 487,723, Mar. 5, 1990, abandoned.

[51] Int. Cl.$^5$ .................... C07C 31/44; C07C 31/42
[52] U.S. Cl. .................... 568/844; 568/812; 568/841
[58] Field of Search .................... 568/812, 844, 841

[56] References Cited

U.S. PATENT DOCUMENTS

| | | | |
|---|---|---|---|
| 2,463,850 | 3/1949 | Brooks | 260/617 |
| 2,714,121 | 7/1955 | Anderson et al. | 260/633 |
| 2,902,519 | 9/1959 | Cosby et al. | 260/633 |
| 3,845,145 | 10/1974 | Wojtowicz et al. | 568/812 |
| 3,859,367 | 1/1975 | Yamamoto et al. | 260/633 |
| 4,496,777 | 1/1985 | Suciu et al. | 568/812 |

FOREIGN PATENT DOCUMENTS

| | | | |
|---|---|---|---|
| 45-22724 | 7/1970 | Japan | 568/844 |
| 0789479 | 12/1980 | U.S.S.R. | 568/844 |
| 569716 | 6/1945 | United Kingdom . | |
| 761212 | 11/1956 | United Kingdom . | |

OTHER PUBLICATIONS

Article on "Chlorohydrins" by Y. T. Liu, F. Richey and J. E. Betso, Ullman's Encyclopedia of Industrial Chemistry, Fifth Edition, vol. A6, (1986), 1986.
Noller, Chemistry of Organic Compounds, Third Edition, Saunders Co., (1965), pp. 815 and 824.

*Primary Examiner*—Werren B. Lone
*Attorney, Agent, or Firm*—F. A. Iskander

[57] ABSTRACT

Described herein is a process for the preparation of chlorohydrins by reacting a concentrated, aqueous solution of hypochlorous acid with at least one unsaturated organic compound having from 2 to about 10 carbon atoms and selected from the group consisting of substituted or unsubstituted olefins and cyclic olefins.

24 Claims, No Drawings

PREPARATION OF CHLOROHYDRINS

This application is a continuation-in-part of pending U.S. application Ser. No. 07/487,723, filed Mar. 5, 1990 abandoned.

This invention relates to an improved process for making chlorohydrins by the reaction of hypochlorous acid with selected unsaturated organic compounds in an essentially aqueous medium. The chlorohydrins are useful as intermediates in the preparation of epoxides.

A widely used epoxide is propylene oxide and it can be prepared from propylene chlorohydrin. The latter in turn is prepared by first forming hypochlorous acid (HOCl) in situ, and then reacting it with propylene. HOCl is prepared in situ by reacting chlorine gas and water. However, this reaction produces an equivalent amount of hydrochloric acid, i.e., $$Cl_2 + H_2O \rightleftharpoons HOCl + HCl$$

When HOCl reacts with propylene an intermediate cyclic chloronium ion is first formed. This ion reacts with water to form propylene chlorohydrin. However, the cyclic chloronium ion can also react with the hydrochloric acid formed in the preparation of HOCl from chlorine gas and water to form 1,2-dichloropropane, an undesirable by-product which may be formed in amounts of as much as about 10%. This by-product must be separated from the desired propylene chlorohydrin, an operation that adds to the cost of making the chlorohydrin.

Attempts have been made to neutralize the hydrochloric acid by the addition of an alkali, such as sodium or calcium hydroxide. However, such a neutralization produces an equivalent amount of a water-soluble inorganic salt. The salt dissolves in water present in the system, producing free chloride. The free chloride in turn reacts with the cyclic chloronium ion producing the same undesirable by-product, i.e., 1,2-dichloropropane.

Therefore, since large amounts of undesirable by-products are produced both from the hydrochloric acid reaction and the product of neutralization of the hydrochloric acid in water, the prior art method of making propylene chlorohydrin by the reaction of HOCl with propylene is highly disadvantageous, inasmuch as it requires costly separation operations and less of the desired propylene chlorohydrin product is formed.

A method to lower by-product formation in the chlorohydrin forming reaction of unsaturated compounds with HOCl is described in U.S. Pat. No. 3,845,145, which issued on Oct. 29, 1974. The hypochlorous acid solution used in the process of the patent is described as being substantially free from chloride. The patent states that the presence of halide ions tends to form undesirable by-Products. To reduce by-product formation, the patent calls for using a particular hypochlorous acid solution. This solution is prepared by extracting an aqueous solution containing sodium chloride and hypochlorous acid at a temperature of +10° to −30° C. with an organic solvent. Methyl ethyl ketone solvent is stated to be of special advantage. The resulting solution of hypochlorous acid in organic solvent is separated from the aqueous phase. The product comprises a solution of hypochlorous acid in organic solvent. This solution of hypochlorous acid in organic solvent is then reacted with an unsaturated organic compound to form the chlorohydrins, the reaction being effected in a solvent medium. According to the patent, it would be advantageous to use an organic solvent reaction medium which is the same as that selected for dissolving the hypochlorous acid, so that only one organic solvent would be needed.

However, the method described in the '145 patent has at least two disadvantages. First, if the HOCl in organic solvent is not immediately used, it must be stored. Storage of the HOCl in organic solvent could lead to reaction between the HOCl and organic solvent resulting in its unacceptability as a reactant. Secondly, the method described in the patent requires that the chlorohydrin forming reaction be carried out in an organic solvent. This certainly adds to the cost of production of the chlorohydrin versus a process which could be conducted in an aqueous medium.

In the present invention, it has been found that chlorohydrins can be prepared by reaction of an unsaturated organic compound and a concentrated aqueous hypochlorous acid solution. The reaction is carried out in an essentially aqueous medium. Thus, no organic solvent medium is required as is needed in the process of U.S. Pat. No. 3,845,145, discussed above. Further, since the hypochlorous acid used in the process of this invention is dissolved in water, there is no problem with reaction between HOCl and organic solvent.

Moreover, the use of the concentrated aqueous solution of hypochlorous acid as a reactant in the process of this invention results in higher concentrations of the product chlorohydrins. Additionally, since the process of this invention is carried out in an aqueous medium, solvent recovery, recycle, etc., is eliminated which results in the elimination of equipment to perform these functions and thus, a more economical process.

A further advantage of the process of this invention is that it can be carried out batch-wise. By contrast, prior art processes, where solvent is used to perform the chlorination reaction, are generally carried out in a continuous manner. Carrying out such a process in a continuous manner requires more equipment and process steps resulting in a costlier product.

Additionally, the use of substantially pure, concentrated aqueous hypochlorous acid solution, in accordance with this invention reduces by-product formation since the hypochlorous acid solution is substantially free of chloride, chlorate, and alkali metal ions.

Still further, in accordance with a preferred embodiment of this invention, it has been found that the addition of a surfactant to the chlorohydrin-forming reaction unexpectedly increases the yield of the chlorohydrin product.

More specifically, this invention is directed to the preparation of chlorohydrins by reacting at least one unsaturated organic compound containing from 2 to about 10 carbon atoms and selected from the group consisting of substituted and unsubstituted olefins and cyclic olefins, the substituents being selected from the group consisting of an alkyl radical, a phenyl radical and an alkylphenyl radical (i.e., tolyl, xylyl or ethylphenyl), each of said radicals being itself optionally substituted with a halide or a hydroxide, with an aqueous hypochlorous acid solution containing at least 10% by weight of hypochlorous acid. The reaction is carried out in an essentially aqueous media. The process may optionally be carried out in the presence of a surfactant.

Any suitable unsaturated compound containing from about 2 to about 10 carbon atoms and meeting the criteria specified above can be used in the process of the invention to prepare the corresponding chlorohydrin. By way of illustration, such unsaturated organic compounds include, but are not limited to, ethylene, propylene, butylene, hexene, cyclohexene, cyclopentene, cyclooctene and mixtures thereof.

Illustrative substituted olefins which may be used in the process of the invention include, but are not limited to, allyl alcohol, allyl chloride, styrene, 4-bromo-1-butene, 3-chloro-1-butene, 3-chloro-2-methylpropene, 1-hexene-3-ol, 3-butene-2-ol, 3-pentene-2-ol, 1-octene-3-ol, and mixtures thereof.

In accordance with the preferred embodiments of the invention, the unsaturated organic compound contains from 2 to 8 carbons and more preferably 2 to 6 carbons. It should become readily apparent of course that by so limiting the number of carbon atoms, the range of substituents on the olefin reactant would be correspondingly restricted. Thus an upper limit of 8 carbons obviously means that the substituent on the olefin can be phenyl but not alkylphenyl. Likewise, an upper limit of 6 carbons precludes the presence of a phenyl substituent on the olefin reactant.

The hypochlorous acid used in the instant process may be characterized as a solution containing greater than 10% by weight of hypochlorous acid, preferably from about 20 to about 65, and most preferably from about 35 to about 55% by weight of hypochlorous acid. The hypochlorous acid solution is substantially free of chloride, chlorate, and alkali metal ions.

The process for producing the hypochlorous acid solution comprises reacting an aqueous alkali metal hydroxide, such as sodium hydroxide, potassium hydroxide, or lithium hydroxide in droplet form with chlorine gas. The reaction is conducted at temperatures high enough to vaporize hypochlorous acid as it is produced. As gaseous mixtures having high concentrations of hypochlorous acid and chlorine monoxide are desired, highly concentrated aqueous solutions of the alkali metal hydroxide are used. Suitable concentrations include those in the range of from about 40 to about 80%, and preferably from about 45 to about 60% by weight of alkali metal hydroxide. A stoichiometric excess of chlorine above that required to form hypochlorous acid with all of the alkali metal hydroxide is used, for example from about 1 to about 20, and preferably from about 5 to about 10 times the stoichiometric proportion of chlorine is employed. Solid particles of alkali metal chloride are also produced during the reaction which have a wide range of particle sizes. The solid particles may be removed by any suitable separation means, for example, by passing the gaseous mixture through a gas filter medium or through a solid separator such as a cyclone.

Now free of solids, the gaseous mixture, which is comprised of hypochlorous acid vapor, chlorine monoxide, chlorine and water vapor, is fed to a condenser. The condenser is operated at temperatures which produce concentrated aqueous solutions of hypochlorous acid without condensing undesirable amounts of chlorine or liquid chlorine monoxide. Suitable temperatures for operating the condensation process include those in the range of from about $-5°$ C. to about $+20°$ C.

The resulting concentrated hypochlorous acid solution so produced will contain from about 35 to about 65 percent by weight of HOCl. It can be diluted with the deionized water to the exact HOCl concentration desired, e.g. 10 percent or higher.

The concentrated hypochlorous acid solution is highly pure and its content of dissolved chlorine is less than about 2% by weight. The concentrated hypochlorous acid solution is essentially free of ionic impurities such as alkali metal, chloride, and chlorate ions. Concentrations of the chloride ion are less than about 50 parts per million; the alkali metal ion concentration is less than about 50 parts per million; and the chlorate ion concentration is no more than about 100 parts per million.

A process for producing hypochlorous acid is described in, for example, U.S. Pat. No. 4,146,578, incorporated in its entirety herein by reference.

The process of this invention is carried out in an essentially aqueous medium at any suitable temperature. For obvious practical reasons, such a temperature is above the freezing point of water but below the decomposition temperature of HOCl. Thus the reaction temperature may range for example from just above the freezing point of water (e.g., about about $1°-2°$ C.) to about $55°$ C., preferably to about $35°$ C. and more preferably to about $15°$ C. Of course, these temperature ranges will require adjustment if the reaction is carried out at under pressure.

One or more surfactants may be included in the process of this invention. Although not critical, the use of a surfactant is desirable, particularly in those instances where the unsaturated organic reactant is highly insoluble in water. The type of surfactant used is not critical. Thus anionic, nonionic, cationic, and amphoteric surfactants may be employed. The anionic surfactants include alkylbenzenesulfonates, alkanesulfonates, x-olefin- sulfonates; cationic surfactants such as quaternary ammonium compounds; nonionic surfactants such as alkyl poly(ethylene glycol) ethers, alkylphenol poly-(ethylene glycol) ethers, fatty acid alkanolamides, and fatty alcohol polyglycol ethers; amphoteric surfactants such as alkylbetaines and alkylsulfobetaines.

The preferred surfactants include sodium dodecylbenzene sulfonate, $C_{14}-C_{16}$ alkyl dimethyl benzyl ammonium chloride, and nonylphenol ethoxylate of 6 to 12 ethylene oxide units, preferably 9 ethylene oxide units. The surfactants are used in any suitable amounts such as from 0.05 to 0.2 parts per every 100 parts by weight of water.

The process of this invention is particularly suited for batch-wise operation, although if desired, it may also be carried out on a continuous basis. In batch operation, the aqueous hypochlorous acid solution is generally fed into a reactor precharged with the unsaturated organic compound, water, and optional additive such as surfactant. The reaction product is then directed to a storage tank or to a second reactor for a subsequent reaction, if desired. The batch process is preferred in that it requires less equipment and is thus more economical then a continuous process although a continuous process may be used, if desired. The order of addition of the unsaturated organic compound, hypochlorous acid solution and water is not critical, and all components may be introduced simultaneously.

In carrying out the reaction according to the invention, the molar ratio of unsaturated organic compound to HOCl is not critical. Neither is the weight ratio of organic compound to water. Thus any suitable ratios or relative proportions may be employed. However, for optimum results, it is preferable to use a molar ratio of unsaturated organic compound to HOCl from about 0.8:1.0 to about 1.3:1.0 and a weight ratio of unsaturated organic compound to water from about 3% to about 30%.

The crude chlorohydrin solution prepared by the process of this invention and optionally containing the surfactant may be converted directly to an epoxide by reaction with a base such as an alkali metal hydroxide. Preferred alkali metal hydroxide includes sodium and potassium hydroxide.

EXAMPLES

The following examples serve to give specific illustrations of the practice of this invention, but they are not intended in any way to limit the scope of the invention. All parts and percentages are by weight unless otherwise specified.

Preparation of Hypochlorous Acid Solution

The following represents a typical process for the preparation of a concentrated aqueous hypochlorous acid solution useful in the process of this invention:

A gaseous mixture containing an average concentration of 180.7 parts by weight of chlorine monoxide, 384.5 parts by weight of $Cl_2$, and 60.3 parts by weight of water vapor was continuously passed through a cyclone separator to remove any entrained solid particles of alkali metal chloride. The solid-free gaseous mixture at a temperature of 85°–90° C. was passed through a vertical shell and tube heat exchanger maintained at a temperature of about 0° C. and a pressure of about 3–4 torr gauge to condense a portion of the chlorine monoxide and substantially all of the water vapor to produce an aqueous hypochlorous acid solution containing 45 to 50% by weight of HOCl. The hypochlorous acid solution had a pH of about 1 and the dissolved chlorine concentration was determined to be about 1% by weight. An uncondensed gas mixture containing an average of 141.9 parts by weight of $Cl_2O$, 384.1 parts by weight of $Cl_2$ and 0.5 parts by weight of water was continuously removed from the condenser. The uncondensed gas mixture was passed through a heat exchanger to raise the temperature to about 100° C. and recycled to a generator used to produce the gaseous mixture of chlorine monoxide.

EXAMPLE 1

Propylene Chlorohydrin Preparation

Excess propylene was bubbled through 135 g. of water, pre-cooled at 1° C., while an aqueous solution of hypochlorous acid (20 g.; 23.3% by weight in water) was added dropwise over a period of seventeen minutes. The reaction temperature was maintained at 1°–3° C. by external cooling during the addition of the hypochlorous acid solution. The reaction was held at <5° C. for fifteen minutes. Sodium chloride (50 g.) was then added to saturate the aqueous solution, and the reaction mixture was extracted with ethyl ether. The separated ether layer was dried with anhydrous magnesium sulfate, filtered, and solvent removed. A clean liquid was obtained. Vapor phase chromatography (V.P.C.) analysis showed the following products were produced and their yields, based on HOCl consumed, are as follows:

| Product | % Yield |
| --- | --- |
| Propylene Chlorohydrin | 97 |
| Propylene Dichloride | 0.21 |

-continued

| Product | % Yield |
| --- | --- |
| Chloroisopropyl Ether | 0.37 |

EXAMPLE 2

Glycerin Monochlorohydrin

Allyl alcohol (10.17 g. 0.172 mol.) was added to it 83 g. of distilled water and cooled to 1° C. An aqueous solution of HOCl (29% by weight in water; 31.2 g.; 0.172 mol.) was added dropwise over a period of eighteen minutes, while the reaction temperature was maintained at <5° C. After the addition was completed, the reaction mixture was held at <5° C. for 30 minutes. A clear, homogeneous solution was obtained. V.P.C. analysis showed the following products were produced and their yields, based on allyl alcohol consumed, are as follows:

| Product | % Yield |
| --- | --- |
| Glycerin Monochlorohydrin | 92 |
| Glycerin Dichlorohydrin | 0.8 |
| Bis-(chlorohydroxylpropyl) ether | 4.9 |

EXAMPLE 3

Glycerin Monochlorohydrin

The reaction of Example 2 was repeated with the following changes: water, 191 g. instead of 83 g. was used, and HOCl, 28.1 g. of 32.1% by weight was used instead of 31.2 g. of 29% by weight. V.P.C. analysis showed the following products were produced and their yields, based on allyl alcohol consumed, are as follows:

| Product | % Yield |
| --- | --- |
| Glycerin Monochlorohydrin | 93.4 |
| Glycerin Dichlorohydrin | 0 |
| Bis-(chlorohydroxylpropyl) ether | 1.5 |

EXAMPLE 4

Glycerin Dichlorohydrin

Allyl chloride (10 g.; 0.13 mol.) was added to 91 g. of distilled water and cooled to 1° C. An aqueous solution of HOCl (32.1% by weight; 21.3 g.; 0.13 mol.) was added dropwise over a period of fifteen minutes, while the reaction mixture was rapidly stirred and the reaction temperature was maintained at <5° C. by external cooling. After the addition was completed, the reaction mixture was held at <5° C. for 30 minutes, warmed to the ambient temperature, and then extracted with methylene chloride. The methylene chloride layer was separated, dried over anhydrous magnesium sulfate, filtered, and solvent removed. A clear liquid was obtained. V.P.C. analysis showed the following products were produced and their Yields, based on allyl chloride consumed, were as follows:

| Product | % Yield |
| --- | --- |
| Dichloropropanol | 89 |
| 1,2,3-Trichloropropane | 1 |

-continued

| Product | % Yield |
| --- | --- |
| Bis-(2,3-dichloropropyl) ether | 1.5 |

EXAMPLE 5

Glycerin Dichlorohydrin

The procedure of Example 4 was repeated except less water, 21 g. instead of 91 g., was used. V.P.C. analysis showed the following products were produced and their yields, based on allyl alcohol consumed, are as follows:

| Product | % Yield |
| --- | --- |
| Dichloropropanol | 83 |
| 1,2,3-Trichloropropane | 2 |
| Bis-(1,2-dichloropropyl) ether | 5 |

EXAMPLE 6

Glycerin Dichlorohydrin

The reaction of Example 4 was repeated with the exception that a nonionic surfactant, nonylphenol ethoxylate (0.063 g.) with 9 ethylene oxide units, was added to the reaction. V.P.C. analysis showed the following products were produced and their yields, based on allyl alcohol consumed, are as follows:

| Product | % Yield |
| --- | --- |
| Dichloropropanol | 92 |
| 1,2,3-Trichloropropane | 1 |
| Bis-(1,2-dichloropropyl) ether | 1.6 |

EXAMPLE 7

Glycerin Dichlorohydrin

The reaction of Example 5 was repeated with the exception that a nonionic surfactant, nonylphenol ethoxylate (0.021 g.) with 9 ethylene oxide unit was added to the reaction. V.P.C. analysis showed the following products were produced and their yields, based on allyl alcohol consumed, are as follows:

| Product | % Yield |
| --- | --- |
| Dichloropropanol | 86 |
| 1,2,3-Trichloropropane | 2 |
| Bis-(1,2-dichloropropyl) ether | 4.7 |

EXAMPLE 8

1-Hexene Chlorohydrin

1-Hexene (10 g.; 0.12 mol.) was added to 163 g. of distilled water and cooled to 1° C. An aqueous solution of HOCl (29.3% by weight; 17.2 g.; 0.096 mol.) was added over a period of thirteen minutes while the reaction mixture was rapidly stirred and the reaction temperature was maintained at <5° C. After the addition was completed, the reaction mixture was maintained at <5° C. for 30 minutes, warmed to ambient temperature, and then 65 g. of sodium chloride was added. A clear organic layer phased out from the aqueous layer was separated. V.P.C. analysis showed the following products were produced and their yields, based on 1-hexene consumed, are as follows:

| Product | % Yield |
| --- | --- |
| 1-Hexene Chlorohydrin | 82 |
| 1,2-Dichlorohexane | 1.7 |
| Bis-(chlorohexyl) Ether | 9.7 |

EXAMPLE 9

1-Hexene Chlorohydrin

The reaction of Example 8 was repeated with the following changes: less distilled water, 90 g. was used instead of 163 g.; less sodium chloride, 38 g. was used instead of 65 g.; and more HOCl, 0.12 mol. was used instead of 0.096 mol. V.P.C. analysis showed the following products were produced and their yields, based on 1-hexene consumed, are as follows:

| Product | % Yield |
| --- | --- |
| 1-Hexene Chlorohydrin | 64 |
| 1,2-Dichlorohexane | 4 |
| Bis-(chlorohexyl) Ether | 22.5 |

EXAMPLE 10

1-Hexene Chlorohydrin

The reaction of Example 9 was repeated with the exception that nonylphenol ethoxylate (0.053 g.) with 9 ethylene oxide was added. V.P.C. analysis showed the following products were produced and their yields, based on 1-hexene consumed, are as follows:

| Product | % Yield |
| --- | --- |
| 1-Hexene Chlorohydrin | 87 |
| 1,2-Dichlorohexane | 0 |
| Bis-(chlorohexyl) Ether | 6.51 |

EXAMPLE 11

1-Hexene Chlorohydrin

The reaction of Example 8 was repeated with the exception that nonylphenol ethoxylate (0.18 g.) with 9 ethylene oxide units was added. V.P.C. analysis showed the following products were produced and their yields, based on 1-hexene consumed, are as follows:

| Product | % Yield |
| --- | --- |
| 1-Hexene Chlorohydrin | 93 |
| 1,2-Dichlorohexane | 0 |
| Bis-(chlorohexyl) Ether | 2.1 |

EXAMPLE 12

1-Hexene Chlorohydrin

The reaction of Example 10 was repeated with the exception that sodium dodecylbenzenesulfate (0.053 g.), an anionic surfactant was added, instead of the nonylphenol ethoxylate. V.P.C. analysis showed the following products were produced and their yields, based on 1-hexene consumed, are as follows:

| Product | % Yield |
|---|---|
| 1-Hexene Chlorohydrin | 81.3 |
| 1,2-Dichlorohexane | 0 |
| Bis-(chlorohexyl) Ether | 14.4 |

EXAMPLE 13

1-Hexene Chlorohydrin

The reaction of Example 10 was repeated with the exception that alkyl dimethyl benzyl ammonium chloride (C14–C16 alkyl; 0.053 g.) was added instead of the nonylphenol ethoxylate. V.P.C. analysis showed the following products were produced and their yields, based on 1-hexene consumed, are as follows:

| Product | % Yield |
|---|---|
| 1-Hexene Chlorohydrin | 88.5 |
| 1,2-Dichlorohexane | 0 |
| Bis-(chlorohexyl) Ether | 7.3 |

EXAMPLE 14

1-Hexene Chlorohydrin

The reaction of Example 10 was repeated with the exception that the reaction temperature was maintained at 45°–51° C. by external heating. V.P.C. analysis showed the following products were produced and their yields, based on 1-hexene consumed, are as follows:

| Product | % Yield |
|---|---|
| 1-Hexene Chlorohydrin | 75.8 |
| 1.0-Dichlorohexane | 0 |
| Bis-(Chlorohexyl) ether | 12.6 |

EXAMPLE 15

Styrene Chlorohydrin

Styrene (10 g.; 0.096 mol.) was added to 288 g. of distilled water and cooled to 1° C. An aqueous solution of HOCl (30% by weight; 16.9 g; 0.096 mol.) was added over a period of thirteen minutes. After the addition was completed, the reaction mixture was held at <5° C. for 30 minutes, warmed to the ambient temperature, and extracted with methylene chloride. The methylene chloride layer was separated, dried with anhydrous magnesium sulfate, filtered, and solvent removed. A clear liquid was obtained. V.P.C. analysis showed the following products were produced and their yields, based on styrene consumed, are as follows:

| Product | % Yield |
|---|---|
| Styrene Chlorohydrin | 77 |
| Chloroacetophenone | 4.5 |
| Bis-(chloroethylphenyl) Ether | 2.6 |

EXAMPLE 16

Styrene Chlorohydrin

The reaction of Example 15 was repeated, except less water, 87 g instead of 288 g., was used. V.P.C. analysis showed the following products were produced and their yields, based on styrene consumed, are as follows:

| Product | % Yield |
|---|---|
| Styrene Chlorohydrin | 64 |
| Chloroacetophenone | 11.8 |
| Bis-(chloroethylphenyl) Ether | 6.7 |

EXAMPLE 17

Styrene Chlorohydrin

The reaction of Example 15 was repeated, with the exception that nonylphenol ethoxylate (0.6 g.) with 9 ethylene oxide units was added. V.P.C. analysis showed the following products were produced and their yields, based on styrene consumed, are as follows:

| Product | % Yield |
|---|---|
| Styrene Chlorohydrin | 79 |
| Chloroacetophenone | 4.2 |
| Bis-(chloroethylphenyl) Ether | 2.4 |

EXAMPLE 18

Styrene Chlorohydrin

The reaction of Example 15 was repeated, with the exception that nonylphenol ethoxylate (0.2 g.) with 9 ethylene oxide units was added. V.P.C. analysis showed the following products were produced and their yields, based on styrene consumed, are as follows:

| Product | % Yield |
|---|---|
| Styrene Chlorohydrin | 69 |
| Chloroacetophenone | 5.7 |
| Bis-(chloroethylphenyl) Ether | 8.4 |

EXAMPLE 19

Cyclohexene Chlorohydrin

Cyclohexene (10 g.; 0.12 mol.) was added to 90 g. of distilled water and cooled to 1° C. HOCl (30% by weight in water; 21 g.; 0.12 mol.) was added over a period of twenty-two minutes, while the reaction mixture was stirred rapidly and the reaction temperature was maintained at <5° C. After the addition was completed, the reaction mixture was held at <5° C. for 1 hour, and warmed to the ambient temperature. 35 g. of sodium chloride were then added to the reaction mixture. It was then extracted with ethyl ether. The ether layer was separated. It was dried over anhydrous magnesium sulfate, filtered, and solvent removed. A clear liquid was obtained. V.P.C. analysis showed the following products were produced and their yields, based on cyclohexene consumed, are as follows:

| Product | % Yield |
|---|---|
| Cyclohexene Chlorohydrin | 91 |
| 1,2-Dichlorohexane | 0 |
| Bis-(chlorocyclohexyl) Ether | 1 |

EXAMPLE 20

Cyclohexene Chlorohydrin

The reaction of Example 19 was repeated with the exception that water, 40 g. was used instead of 90 g. V.P.C. analysis showed the following products were produced and their yields, based on cyclohexene consumed, are as follows:

| Product | % Yield |
| --- | --- |
| Cyclohexene chlorohydrin | 86 |
| 1,2-Dichlorohexane | 0 |
| Bis-(chlorocyclohexyl) Ether | 1.6 |

EXAMPLE 21

Propylene Chlorohydrin

Excess propylene was bubbled through 191 g. of water at ambient temperature while HOCl (21 g.; 30.6% by weight in water) was added dropwise over a period of twelve minutes. The bubbling of propylene gas was stopped when all the HOCl was reacted, and the reaction temperature was recorded as 38° C. 70 g. of sodium chloride were added, and the reaction mixture was extracted with ethyl ether. The separated etheral layer was dried over anhydrous magnesium sulfate, filtered, and solvent removed. A clear liquid was obtained. V.P.C. analysis showed the following products were produced and their yields, based on HOCl consumed, are as follows:

| Product | % Yield |
| --- | --- |
| Propylene Chlorohydrin | 93.5 |
| Propylene Dichloride | Trace |
| Cloroisopropyl Ether | 0.70 |

EXAMPLE 22

1,2-Epoxyhexane

The emulsion prepared from 1-hexene (20 g.; 0.24 mol.) and nonylphenol ethoxylate (0.13 g.) with 9 ethylene oxide in distilled water (185 g.) was rapidly stirred. To it was added dropwise an aqueous HOCl solution (32.5% by weight; 38.8 g; 0.24 mol.) over a period of fifteen minutes. The reaction temperature was maintained at <5° C. After the addition was completed, the reaction mixture was held at 3°-5° C. for fifteen minutes. 50% of sodium hydroxide (17.3 g.; 0.22 mol.) was then added. The addition was completed over a period of eight minutes while the reaction temperature was maintained at <3° C. The reaction mixture was post reacted at <3° C. for 2 hours and at the ambient temperature for another 30 minutes, saturated with sodium chloride (70 g.) and then extracted with methylene chloride. The methylene chloride layer was separated, dried over anhydrous magnesium sulfate, filtered, and solvent removed. A clear liquid was obtained and distilled under reduced pressure to give a clear liquid of 1,2-epoxyhexane (16.82 g.; 0.168 mol.). Boiling point of 73°-73° C./55 mm, at 70% yield.

COMPARATIVE EXAMPLE

Preparation of 1-Hexene Chlorohydrin from Chlorine gas in Water in a Batch Reactor For comparison, 1-hexene (10 g.; 0.12 mol.) was added to 105 g of distilled water, rapidly stirred, and cooled to 1° C. Chlorine gas (0.825 g./min.) was bubbled through the reaction mixture from the bottom of the reactor while the reaction temperature was maintained at 3°-4° C. The bubbling of chlorine gas was stopped 10.3 minutes later, and the reaction mixture was post reacted at 3°-4° C. for another 30 minutes. Sodium chloride (33 g.) was added, and the clear organic layer separated from the aqueous layer. The clear liquid was collected. V.P.C. analysis showed the following products were produced and their yields, based on 1-hexene consumed, are as follows:

| Product | % Yield |
| --- | --- |
| 1-Hexene Chlorohydrin | 2.56 |
| 1,2-Dichlorohexane | 62.8 |

What is claimed is:

1. A process for the preparation of a chlorohydrin which comprises reacting at least one unsaturated organic compound containing from 2 to about 10 carbon atoms and selected from the group consisting of substituted and unsubstituted olefins and cyclic olefins, the substituents being selected from the group consisting of an alkyl radical, a phenyl radical and an alkylphenyl radical, each of said radicals being itself unsubstituted or substituted with a halide or a hydroxide, with an aqueous hypochlorous acid solution containing more than 10% by weight of hypochlorous acid and being substantially free of chloride, chlorate, and alkali metal ions, said process being conducted in an essentially aqueous medium.

2. A process as defined in claim 1 wherein the organic compound is propylene.

3. A process as defined in claim 1 wherein the organic compound is allyl alcohol.

4. A process as defined in claim 1 wherein the organic compound is allyl chloride.

5. A process as defined in claim 1 wherein the organic compound is 1-hexene.

6. A process as defined in claim 1 wherein the organic compound is cyclohexene.

7. A process as defined in claim 1 wherein the organic compound is styrene.

8. A process as defined in claim 1 wherein the hypochlorous acid solution contains from about 20 to about 65% by weight of hypochlorous acid.

9. A process as defined in claim 8 wherein the hypochlorous acid solution contains from about 35 to about 55% by weight of hypochlorous acid.

10. A process as defined in claim 1 which is conducted in the presence of an anionic, nonionic, cationic, or amphoteric surfactant.

11. The process of claim 1 wherein said reaction is carried out at a temperature above the freezing point of water up to about 35° C.

12. The process of claim 1 wherein from about 3 to about 30 parts of said unsaturated organic compound are used per every 100 parts by weight of water and the molar ratio of said unsaturated organic compound to said hypochlorous acid ranges from about 0.8:1.0 to about 1.3:1.0.

13. A process for preparing a chlorohydrin which comprises reacting an unsubstituted or substituted olefin or cyclic olefin having 2 to 8 carbon atoms and in which the substituent is selected from the group consisting of an alkyl radical, a phenyl radical and an alkylphenyl radical, each of said radicals being itself unsubstituted or substituted with a halide or a hydroxide, with an aqueous hypochlorous acid solution containing from about 20 to about 65 percent by weight of hypochlorous acid and being substantially free of chloride, chlorate and alkali metal ions, said reaction being carried out in an essentially aqueous medium.

14. The process of claim 13 wherein said reaction is carried out at a temperature above the freezing point of water up to about 35° C.

15. The process of claim 14 wherein said unsaturated organic compound is propylene.

16. The process of claim 14 wherein said reaction is carried out in the presence of an anionic, nonionic, cationic or amphoteric surfactant.

17. The process of claim 16 wherein from about 3 to about 30 parts of said unsaturated organic compound are used per every 100 parts by weight of water.

18. The process of claim 17 wherein the molar ratio of said unsaturated organic compound to said hypochlorous acid ranges from about 0.8:1.0 to about 1.3:1.0.

19. The process of claim 18 wherein said unsaturated organic compound contain 2 to 6 carbon atoms and said reaction ranges from above the freezing point of water to about 15° C.

20. The process of claim 19 wherein said hypochlorous acid solution contains from about 35 to about 55% by weight of hypochlorous acid.

21. The process of claim 20 wherein said surfactant is selected from the group consisting of sodium dodecylbenzene sulfonate, $C_{14}$–$C_{16}$ alkyl dimethyl benzyl ammonium chloride and nonylphenol ethoxylate of 6 to 12 ethylene oxide units.

22. A process for the preparation of a chlorohydrin which comprises the following steps:
(i) forming a hypochlorous acid solution from a gaseous mixture of chlorine monoxide, hypochlorous acid vapor, chlorine, and water vapor, by condensing the gaseous mixture, at a temperature of from about 5° C. to about +20° C., and
(ii) reacting the hypochlorous acid solution with at least one unsaturated organic compound containing from 2 to about 10 carbon atoms selected from the group consisting of substituted and unsubstituted olefins and cyclic olefins, the substituents being selected from an alkyl radical, a phenyl radical and an alkylphenyl radical, each of said radicals being itself unsubstituted or substituted with a halide or a hydroxide.

23. A process as defined in claim 22 wherein the hypochlorous acid solution contains from about 20 to about 60% by weight of hypochlorous acid.

24. A process as defined in claim 23 wherein the hypochlorous acid solution contains from about 35 to about 55% by weight of hypochlorous acid.

* * * * *

UNITED STATES PATENT AND TRADEMARK OFFICE
CERTIFICATE OF CORRECTION

PATENT NO. : 5,146,011

DATED : September 8, 1992

INVENTOR(S) : Ming Shen and John A. Wojtowicz

It is certified that error appears in the above-identified patent and that said Letters Patent is hereby corrected as shown below:

In Column 14, line 17, delete "5°C" and insert -- -5°C --.

Signed and Sealed this

Twenty-sixth Day of October, 1993

*Attest:*

BRUCE LEHMAN

*Attesting Officer*   Commissioner of Patents and Trademarks